United States Patent [19]

Herbold

[11] 4,281,462
[45] Aug. 4, 1981

[54] CALLIPER SYSTEM FOR LAYING OUT STIRRUPS USED IN LOWER EXTREMITY ORTHOSIS

[76] Inventor: Daniel J. Herbold, 120 Destrehan St., Destrehan, La. 70047

[21] Appl. No.: 80,046

[22] Filed: Sep. 28, 1979

[51] Int. Cl.³ ............................. G01B 3/00; B25H 7/04
[52] U.S. Cl. ..................................... 33/191; 33/174 D
[58] Field of Search ................. 33/189, 191, 192, 288, 33/203.2 D, 161, 174 D, 203.17

[56] References Cited

U.S. PATENT DOCUMENTS

| | | | |
|---|---|---|---|
| 2,581,021 | 1/1952 | Jacobsen et al. | 33/288 |
| 2,599,819 | 6/1952 | Fisher | 33/191 |
| 2,972,189 | 2/1961 | Holub | 33/203.2 X |
| 3,151,396 | 10/1964 | Junkins | 33/288 |
| 3,345,755 | 10/1967 | Fexebee | 33/191 |
| 3,583,823 | 6/1971 | Eaton | 33/191 |

Primary Examiner—William D. Martin, Jr.
Attorney, Agent, or Firm—C. Emmett Pugh & Associates

[57] ABSTRACT

An accurate mechanical method and associated calliper for determining the vertical and longitudinal center lines and the mid-point between joint holes in the laying out of a stirrup for use in the foundation of a lower extremity orthosis. The calliper comprises an assembly with three main parts: a floating, calibrated main bar containing two lateral internal springs of equal tension connected to a center punch or marking pin, and two end bars of equal size connected to the other ends of the internal springs, which end bars slide in and out of the main floating bar. Each end bar includes a pin which attaches it to the main bar spring, a stirrup dowel and a scale to be used for inter alia measuring varus or valgus deformities of the ankle. The assembly is placed on a stirrup by inserting the stirrup dowels on the two end bars into the joint holes on the stirrup, thus positioning the main bar for measurement and marking purposes. The center point is marked by, for example, striking the center marking pin with a hammer, which center point is used to determine the bend lines for the stirrup which are then used for appropriately bending the stirrup into the configuration desired for a particular user. The pins on the end bars can also be used if desired for marking the defining points of the stirrup's vertical or lateral axis.

14 Claims, 4 Drawing Figures

CALLIPER SYSTEM FOR LAYING OUT STIRRUPS USED IN LOWER EXTREMITY ORTHOSIS

BACKGROUND OF THE INVENTION

1. Field of the Invention

The present invention relates to a method of laying out a foundation stirrup for a lower extremity orthosis so that the mechanical axis of the stirrup coincides with the anatomical ankle joint and to a calliper useful therein.

The laying out of a foundation stirrup involves the finding of two essential points on the stirrup: the vertical and longitudinal center lines and the mid-point between the stirrup joint holes. When these points have been located on the stirrup, measurements can be taken from the mid-point to locate exactly where the stirrup should be bent in order to fit the orthosis assembly. For patients with a varus or valgus deformity (ankle turned in or out), the deformity needs to be noted on the stirrup when measuring for the bend points in order to assist in the correction of the deformity.

2. Description of the Prior Art

There is no known prior art directly related to the mechanical or automatic measuring of a stirrup to determine its bend points or lines. Devices are known for the correction and improvement of faulty foot posture in a patient through alignment of the feet by measurement of the degree of fault found in the patient's feet, for the purpose of making a wedge for insertion into a corrective shoe; see U.S. Pat. No. 2,492,059 to G. Ogden issued Dec. 20, 1949. Stirrups and the orthotic devices for which they comprise the foundation of are, of course, known as well, see e.g. U.S. Pat. No. 3,732,861 to H. Lehneis, issued May 15, 1973.

The conventional prior art tools used to lay out a stirrup for measurement are a ruler, grease pencil and a straight edge. For a normal foot, the vertical (lateral) and longitudinal center lines are layed out with the ruler and pencil and the mid-point between the joint holes of the stirrup is thus designated. Where a varus or valgus deformity is present, the stirrup must be manually measured in this fashion so that it may be off-set to one side of the foot or the other when bent. A center hole, either at the intersection of the vertical and longitudinal center-lines, or off-set in the case of a deformity, is then drilled. In order to measure the bend points and form the stirrup, the medial lateral width of the shoe at the heel breast is measured and increased by a width of an inch. This dimension is then manually marked equally on each side of the drilled center hole. The stirrup is then transferred to a stirrup bender in order to form the stirrup bends from the measurement taken.

Laying out a stirrup in the above mentioned manner is very time consuming, tedious and often inaccurate, particularly under the pressure of a large volume of work to be completed.

If the stirrup is not laid out correctly, the following problems often arise: binding and excessive wear at the mechanical joint, rapid tiring of the patient's leg due to the muscular effort the patient must expend in trying to overcome the defective mechanical joint, and even temporary or permanent damage to the patient's limb.

SUMMARY DISCUSSION OF THE INVENTION

The present invention utilizes a calliper having an assembly of two bars which slide in and out of a main bar, the end bars being attached to the main bars by means of for example two internal springs extending laterally from a center pin in the main bar to a pin near the end of each end bar. Each end bar has a dowel extending down from its underside. The assembly is fitted over an unbent, flat stirrup by placing the end bar dowels into the stirrup joint holes. The two internal springs being of equal tension, the floating main bar is automatically thus positioned in the exact center of the stirrup. The two pins on the end bars and the pin in the main bar line up automatically on the center-line of the joint holes, and thus the calliper assembly of the invention finds the exact vertical and longitudinal center-lines and the mid point between the joint holes on the stirrup. The assembly can be adjusted to accomodate stirrup sizes ranging from, for example, six inches to ten-and-a-quarter inches (6" to 10¼"). By utilizing the scales on the front of the end bars, the necessary degree of off-set for positioning the adjusted center hole" in the case of a valgus or varus deformity can be measured. These end bar scales also enable the invention to be used without the internal main bar springs. One the "stirrup calliper" is placed on a stirrup and the floating main bar is in position, thumb screws on the main bar are locked down and a soft-face hammer is then used to tap lightly the center pin punch to mark the center hole and, if desired, also the lateral axis on the stirrup by using end pin punches.

Applicant's "Stirrup Calliper" thus provides an easily-utilized and highly accurate mechanical means for taking and marking automatic stirrup measurements which otherwise must be done laboriously by hand, subject to the inaccuracies of human error.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein.

DETAILED DESCRIPTION OF THE PREFERRED EMBODIMENT

Figure 1:
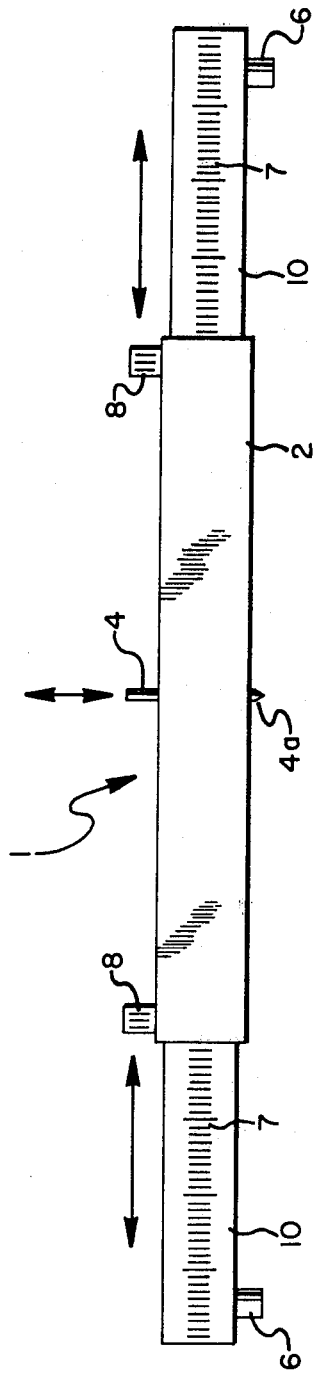
FIG. 1 is an external, side view of the "stirrup calliper" assembly used in the preferred embodiment of the present invention.
Figure 2:
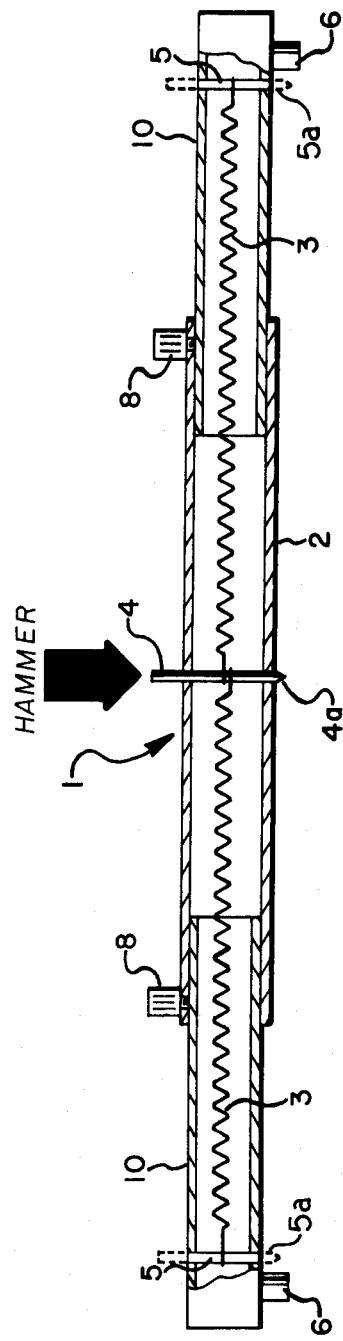
FIG. 2 is an internal, cross-sectional, side view of the "stirrup calliper" assembly of FIG. 1 showing the connection of the end bars to the floating center bar by means of the lateral internal springs.
Figure 3:
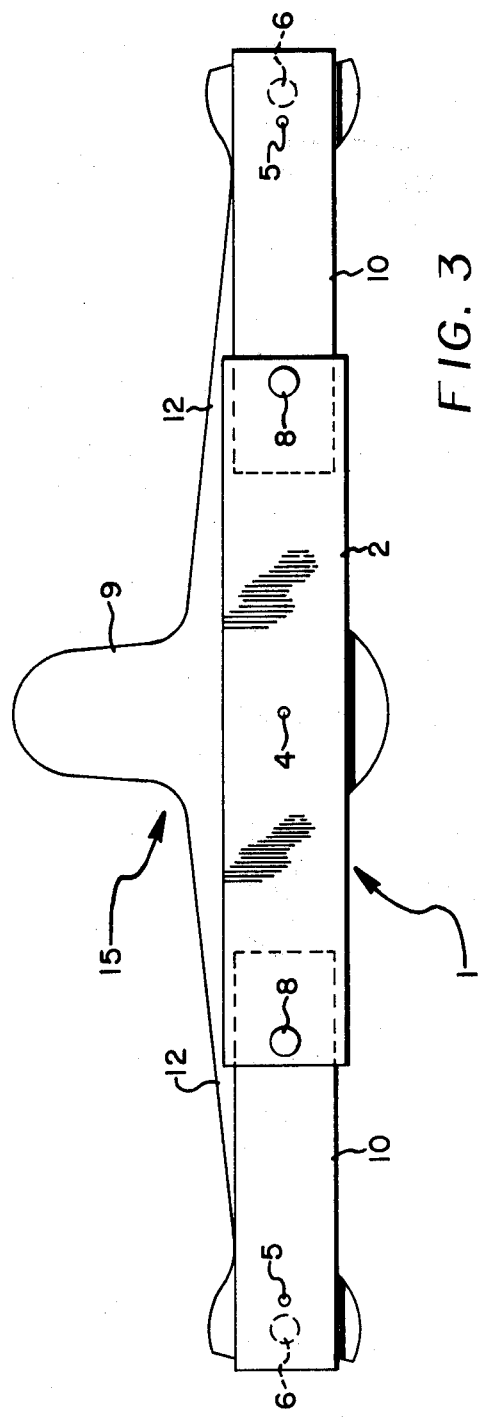
FIG. 3 is a top view of the "stirrup calliper" assembly of FIG. 1 placed atop an exemplary nine-and-a-half inch (9½") unbent stirrup for measurement purposes.

As shown in the side views of FIGS. 1 and 2 and the top view in FIG. 3, the main floating bar 2 of the exemplary preferred embodiment of the calliper 1 is a hollow rectangular tube approximately 5 3/16" in width, ¾41 in height and an inch in depth. Extending point downwardly through the center of the main bar 2 is a metal marking or punch pin of approximately 1/16" diameter having a marking point 4a. Two thumb screws 8 are attached to the top of the main bar 2, one at either end as shown best in the cross-sectional view of FIG. 2.

Two lateral springs 3 are attached at their proximal ends to the center pin 4 in the main bar 2 and extend out from either side. Both springs 3 are of equal tension.

Each end bar 10 is also a hollow rectangular tube of slightly smaller dimension than the main floating bar 3 and approximately 3⅜" in width. The opposed, extended end bars 10 nest and fit inside the open ends of the floating main bar 2 extending out freely, as indicated by the arrows in FIG. 1. Each end bar 10 has a pin 5 running downwardly through it about three-quarters of the way to the end of the bar 10.

The distal end of each spring 3 is attached to its respective end bar pin 5. Rather than as illustrated, the two end bar pins 5, like the main bar center pin 4, can be made to extend out from the bottoms and tops of the end bars 10 the same distance (see lined phantom additions 5a) and then also be used as marking or punch pins 5a for setting and marking the lateral center-line of the stirrup. The cross-sectional view of FIG. 2 best illustrates the internal, telescoping or nesting assembly of the three bars 2, 10 via the two springs 3. A dowel 6 approximately ⅜" in diameter extends downwardly from each end of the end bars 10. These anchoring dowels 6 are positioned next to the end bar pins 5 and extend downwardly approximately 3/32 of an inch further than do the pins 5 if they were made to also function as marking pins 5a.

A measurement scale 7 is etched into the front of each of the end bars 10, as seen in FIG. 1. By sliding the two end bars 10 in or out of the main bar 2 as needed, the entire calliper assembly can be adjusted to accomodate stirrup sizes ranging from 6" to 10¼'.

As shown in FIG. 3, the entire calliper assembly is placed atop a flat, unbent stirrup 15 by means of placing the anchoring dowels 6 extending downward from each of the end bars 10 into the two joint holes 13 at either ends of the flat stirrup 15, anchoring the two end bars 10 to the stirrup 15. Once the assembly is so in place atop the stirrup 15, the floating main bar 2 is automatically positioned uner the equal actions of the springs 3 in the exact center of the stirrup 15, with the center pin 4 pinpointing the location of the center-point on the stirrup 15. The exact, vertical, center-line on the stirrup 15 is thus determined. The center pin 4 also aligns automatically with the two end bar pins 5, thus determining the longitudinal center-line on the stirrup 15.

If a varus or valgus deformity exists which the stirrup 15 is to correct, measurements to place the mid-point between the joint holes determined by the center pin 4 off-centered to the necessary degree can be taken with the use of the calibrating scales 7 on the end bars 10. The thumb screws 8 on the main bar 2 are then locked down to securely clamp the main bar 2 to the end bars 10.

A soft-face hammer (note FIG. 2) is then used to tap lightly on the center pin 4, driving it vertically downwardly to physically mark the mid-point 11 on the tongue section 9 of the stirrup 15 as measured between the joint holes 13, and also to tap on the end pins 5 (if they are made for marking) to mark the points defining the vertical or lateral center-line of the stirrup 15.

The "stirrup calliper" 1 is then removed from the stirrup 15 and measurements can be taken from the mid-point 11 determined and marked by the "stirrup calliper" 1 along the lateral center-line of the stirrup 15 to find the bending lines 14, 16 for the stirrup arms 12.

The "stirrup calliper" 1 can also function without the two internal springs 3 simply by placing the assembly onto the stirrup is in the same manner as would be done with the springs and using the measurement scales 7 to determine the exact center placement of the main bar 2. The scales 7 can of course also be used to double-check the proper center placement of the main floating bar 2 by the spring 3, and then used as a guide for the proper placement should the springs system not be properly working.

Figure 4:
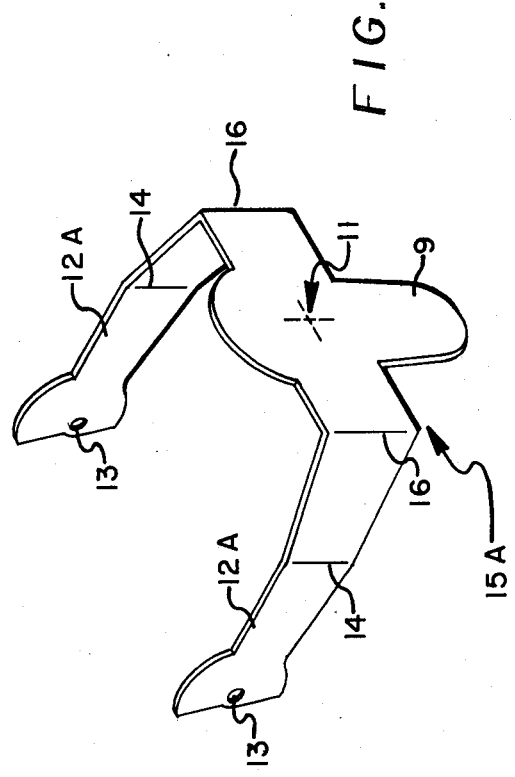
FIG. 4 is an isometric view of the completed, bent stirrup after the measurements have been taken and marked, the "stirrup caliper" removed and the stirrup properly bent into position for use on the patient.

After the bend lines 14, 16 have been determined, the arms 12 of the stirrup 15 are bent into the desired configuration, all as well known in the prior art, to produce the bent arm 12A of the final bent stirrup 15A shown is FIG. 4. The bent stirrup in then ready for final, ultimate use by the patient as a lower extremity orthosis. For a further understanding of the details of the bending aspects of the final stirrup 15A, reference is had to pages 244-248 of the medical text "A Manual of Lower Extremities Orthothics" published by Charles C. Thomas, Banerstone House, (Springfield, IL) written by Clausen F. Englad, et al and edited by Miles H. Anderson, which text is incorprated herein by reference.

Because of the varying embodiments that may be made within the scope of the inventive concept herein taught and because many modifications may be made in the embodiment detailed herein in accordance with the descriptive requirements of the law (such as shape of the three bars), it is to be understood that the details herein are to be interpreted as illustrative and not in a limiting sense.

What is claimed is:

1. A method of making an orthosis stirrup from a flat, piece of bendable stirrup material having joint holes at either end for use in a lower extremity orthosis, comprising the following steps:
    (a) providing a stirrup calliper having two end sections and a moveable central section carrying a marking device and being laterally moveably connected between said two end sections, said two end sections having protruding anchoring means protruding down from said end sections for anchroing said end sections to the stirrup joint holes;
    (b) placing said calliper on the flat stirrup material and inserting said protruding anchoring means into the joint holes and thereby anchoring said anchoring means to the stirrup joint holes;
    (c) centrally locating said marking device over the desired center position of the flat stirrup material off-set, if any, as desired;
    (d) using said marking means to mark the center position of the stirrup material off-set, if any, as desired;
    (e) using the marked position as a base for determining the bend lines for the arms of the stirrup; and
    (f) bending up the arms of the stirrup at the bend lines determined in step "e" to form the stirrup.

2. The method of claim 1, wherein said marking device is a vertically moveable pin, and wherein in step "d" there is further included the step of striking the head of said pin to physically mark the surface of the stirrup.

3. The method of claim 1, wherein there is further included between steps "c" and "d" the step of locking said central section to said end sections to prevent any further relative lateral movements between them after said central section has been appropriately positioned.

4. The method of claim 1, wherein in step "a" said caliper is further provided with spring means for resiliently connecting said central section to said end sections with equal, opposing forces, and wherein step "e"

is performed by the step of said spring means resiliently pulling and positioning said central section centrally with respect to said end sections by means of the equalizing of said equal, opposing forces.

5. The method of either of claims 1 or 4, wherein in step "a" said calliper is provided with calibrating scale means for indicating the relative position of said moveable central section with respect to said end sections, and wherein step "c" further includes the step of using said scale means to manually position said moveable central section to achieve a desired off-set from the true center position of the stirrup.

6. The method of claim 1 wherein there is included after step "e" the futher step of bending up the arms of the stirrup at the bend lines determined in step "e".

7. A measuring and marking calliper for determining and relatively marking the center point between two spaced elements on an item, comprising:

two opposed, extended, end sections; and a movable central section carrying a marking device and being laterally movably connected between said two end sections, said two end sections having anchoring means for anchoring said end section to the two spaced elements, said movable central section being laterally movable with respect to said end sections to position said marking device relative to the center point between the two spaced elements, said cenral section being of tubular construction open at both ends, and said end sections being of like tubular construction but of smaller cross sectional dimension and being slidably nestably positioned in the opposing open ends of said central section;

spring means connected between said central section and said end sections for resiliently connecting said central section to said opposed, extended end sections with equal, opposing forces, said spring means resiliently pulling and positioning said central section centrally with respect to said end sections by means of the equalizing of said equal, opposing forces, said marking device being usable to mark the center position between the two spaced elements off-set, if any, as desired, said marking device being a vertically movable pin extending down through said central section, said spring means being connected at its proximal ends to said pin.

8. The calliper of claim 7, wherein said marking device is a vertically movable pin having tip means for physically marking the surface of the item when the pin is moved downwardly against it.

9. The calliper of claim 7, wherein there is further included locking means associated with said central section for locking said central section to said end sections to prevent any further relative lateral movements between them after said central section has been appropriately positioned.

10. The calliper of claim 7 wherein there is further provided calibrating scale means for indicating the relative position of said movable central section with respect to said end sections, said scale means being usable to manually position said movable central section to achieve a desired off-set from the true center position between the to spaced elements on the item being marked.

11. The calliper of claim 7 wherein said end sections also each have a vertically movable marking pin extending down through said end section toward its far end and wherein said spring means is connected at its distal ends to said end section marking pins.

12. The calliper of claim 7 wherein said tubular construction has a quadrilateral cross-section.

13. The calliper of claim 7, wherein said anchoring means are protruding circular dowels extending down from the bottoms of said end sections.

14. The calliper of claim 7, wherein said spring means comprises two separate, identical springs, each internally located within said central section and in one of said end sections.

* * * * *